US00PP35815P2

(12) United States Plant Patent
Mathey

(10) Patent No.: US PP35,815 P2
(45) Date of Patent: May 21, 2024

(54) ***HYDRANGEA* PLANT NAMED 'SMNHMC'**

(50) Latin Name: *Hydrangea macrophylla*
Varietal Denomination: SMNHMC

(71) Applicant: Megan M. Mathey, Holland, MI (US)

(72) Inventor: Megan M. Mathey, Holland, MI (US)

(73) Assignee: STRING MEADOW NURSERY, INC., Grand Haven, MI (US)

( * ) Notice: Subject to any disclaimer, the term of this patent is extended or adjusted under 35 U.S.C. 154(b) by 0 days.

(21) Appl. No.: 18/239,873

(22) Filed: Aug. 30, 2023

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 6/48; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Hydrangea* plant named 'SMNHMC', characterized by its relatively compact, upright and outwardly spreading plant habit; vigorous growth habit; strong and sturdy stems; dark green-colored leaves; freely and remontant flowering habit with numerous panicles per plant; large mophead inflorescences with semi-double sterile flowers that are light purplish pink in color; and good garden performance.

2 Drawing Sheets

Figure 1:
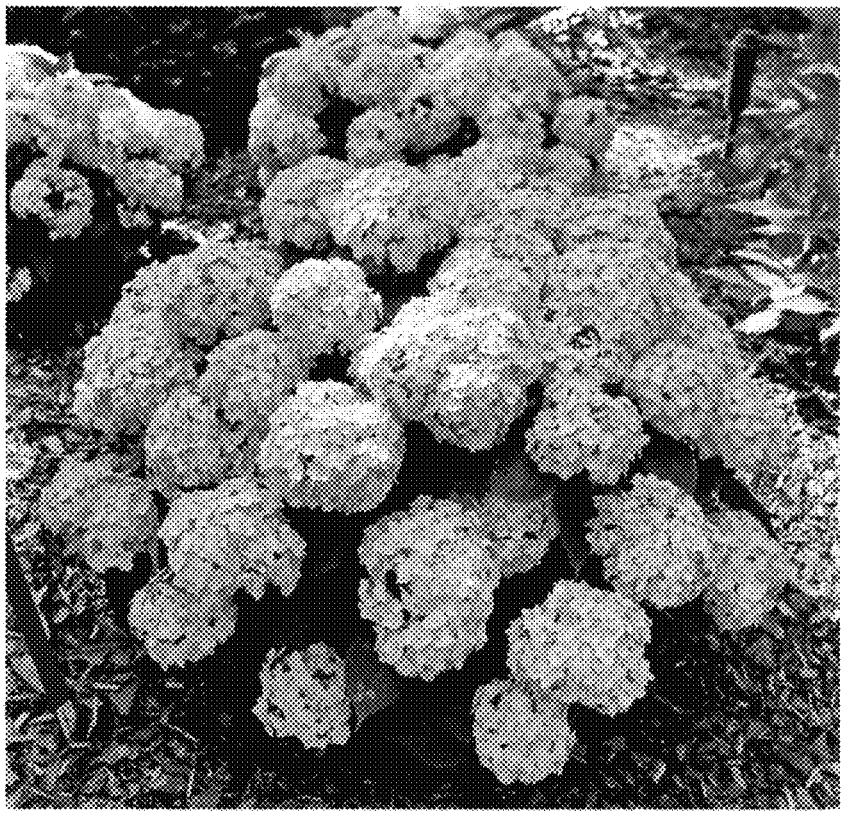

Botanical designation: *Hydrangea macrophylla.*
Cultivar denomination: 'SMNHMC'.

BACKGROUND OF THE INVENTION

The present invention relates to a new and distinct *Hydrangea* plant, botanically known as *Hydrangea macrophylla*, commonly referred to as Mophead or Bigleaf *Hydrangea* and hereinafter referred to by the name 'SMNHMC'.

The new *Hydrangea* plant is a product of a planned breeding program conducted by the Inventor in Grand Haven, Michigan. The objective of the breeding program was to develop compact and remontant flowering *Hydrangea* plants with strong stems and large and attractive inflorescences.

The new *Hydrangea* plant originated from a cross-pollination in 2017 of *Hydrangea macrophylla* 'SMHMTAU' , disclosed in U.S. Plant Pat. No. 27,035, as the female, or seed parent and a proprietary selection of *Hydrangea macrophylla* identified by the name 'Centaurus', not patented, as the male, or pollen, parent. The new *Hydrangea* plant was discovered and selected by the Inventor as a single flowering plant from within the progeny of the stated cross-pollination in a controlled environment in Grand Haven, Michigan in 2018.

Asexual reproduction of the new *Hydrangea* plant by softwood cuttings in a controlled environment in Grand Haven, Michigan since 2018 has shown that the unique features of this new *Hydrangea* plant are stable and reproduced true to type in successive generations of asexual reproduction.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNHMC'. These characteristics in combination distinguish 'SMNHMC' as a new and distinct *Hydrangea* plant:

1. Relatively compact, upright and outwardly spreading plant habit.
2. Vigorous growth habit.
3. Strong and sturdy stems.
4. Dark green-colored leaves.
5. Freely and remontant flowering habit with numerous panicles per plant.
6. Large mophead inflorescences with semi-double sterile flowers that are light purplish pink in color.
7. Good garden performance.

Plants of the new *Hydrangea* differ from plants of the female parent, 'SMHMTAU', in the following characteristics:

1. Plants of the new *Hydrangea* have stronger and sturdier stems than plants of 'SMHMTAU'.
2. Sterile flowers of plants of the new *Hydrangea* are semi-double types whereas sterile flowers of plants of 'SMHMTAU' are single types.
3. Sepals of sterile flowers of plants of the new *Hydrangea* are lighter purplish pink in color than sepals of sterile flowers of plants of 'SMHMTAU'.

Plants of the new *Hydrangea* differ from plants of the male parent, 'Centaurus', in the following characteristics:

1. Plants of the new *Hydrangea* have larger mophead inflorescences whereas plants of 'Centaurus' have smaller lacecap inflorescences.
2. Sterile flowers of plants of the new *Hydrangea* are semi-double types whereas sterile flowers of plants of 'Centaurus' are single types.

Plants of the new *Hydrangea* can be compared to plants of *Hydrangea hybrida* 'SMNHSME', disclosed in U.S. Plant Pat. No. 34,327. In side-by-side comparisons, plants of the new *Hydrangea* differed primarily from plants of 'SMNHSME' in the following characteristics:

1. Plants of the new *Hydrangea* are more compact than plants of 'SMNHSME'.
2. Sterile flowers of plants of the new *Hydrangea* are semi-double types whereas sterile flowers of plants of 'SMNHSME' are single types.
3. Sepals of sterile flowers of plants of the new *Hydrangea* are darker purplish pink than sepals of sterile flowers of plants of 'SMNHSME'.
4. Sepal margins of sterile flowers of plants of the new *Hydrangea* are entire whereas sepal margins of sterile flowers of plants of 'SMNHSME' are serrulate.
5. Flowers of plants of the new *Hydrangea* do not readily respond to "blueing" whereas flowers of plants of 'SMNHSME' are very responsive to "blueing" treatments.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet (FIG. 1) comprises a top perspective view of a typical flowering plant of 'SMNHMC' growing in an outdoor nursery.

Figure 2:
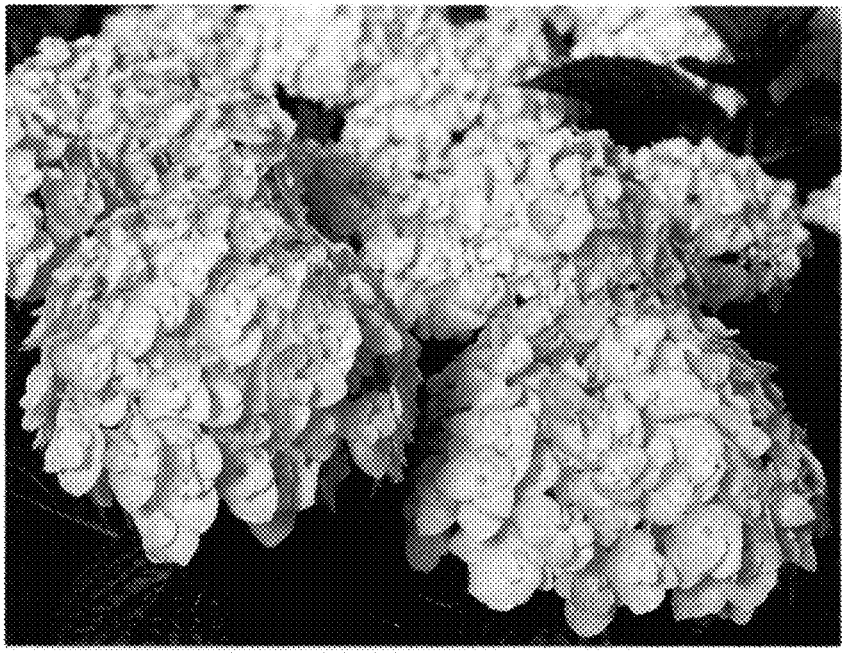

The photograph on the second sheet (FIG. 2) is a close-up view of flowering plant of 'SMNHMC'.

DETAILED BOTANICAL DESCRIPTION

Plants used for the following description were grown during the early summer in three-gallon containers in a polyethylene-covered greenhouse in Grand Haven, Michigan and under cultural practices typical of commercial *Hydrangea* production. During the production of the plants, day temperatures ranged from 18C to 27C and night temperatures ranged from 5C to 10C. Plants of the new *Hydrangea* were three years old when the photographs and description were taken. Plants of the new *Hydrangea* are typically not responsive to treatments of aluminum sulfate to "blue" the inflorescences. In the following description, color references are made to The Royal Horticultural Society Colour Chart, 2015 Edition, except where general terms of ordinary dictionary significance are used.

Botanical description: *Hydrangea macrophylla* 'SMNHMC'.

Parentage:

*Female, or seed, parent.*—*Hydrangea macrophylla* 'SMHMTAU', disclosed in U.S. Plant Pat. No. 27,035.

*Male, or pollen, parent.*—Proprietary selection of *Hydrangea macrophylla* identified with the name 'Centaurus', not patented.

Propagation:

*Type cutting.*—By softwood cuttings.

*Time to initiate roots, summer.*—About 18 days at temperatures about 18C to 27C.

*Time to produce a rooted young plant, summer.*—About 60 days at temperatures about 18C to 27C.

*Root description.*—Fine to thick; fibrous; typically white and brown in color, actual color of the roots is dependent on substrate composition, water quality, fertilizers, substrate temperature and age of roots.

*Rooting habit.*—Freely branching; medium density.

Plant description:

*Plant form and growth habit.*—Perennial deciduous shrub; relatively compact, upright to outwardly spreading plant habit; broad and uniformly mounded inverted triangle; strong and sturdy lateral branches; freely branching habit with about 40 lateral branches developing per plant; vigorous growth habit and moderate to rapid growth rate.

*Plant height.*—About 41.3 cm.

*Plant diameter or area of spread.*—About 72.6 cm.

*Lateral branches.*—Length: About 38 cm. Diameter: About 6 mm. Internode length: About 6 cm. Texture: Smooth, glabrous. Strength: Strong, sturdy. Aspect: About 60 to 80 degrees from vertical. Lenticels: Density: About three per cm. Color: Close to 177A. Color, developing: Close to 144B. Color, developed: Close to 144B; when woody, close to 199B.

Leaf description:

*Arrangement.*—Opposite, simple.

*Length.*—About 12.75 cm.

*Width.*—About 7.8 cm.

*Shape.*—Elliptic.

*Apex.*—Acuminate.

*Base.*—Cuneate.

*Margin.*—Serrulate.

*Texture and luster, upper and lower surfaces.*—Glabrous, somewhat coriaceous; prominent venation on lower surface; glossy.

*Venation pattern.*—Pinnate.

*Color.*—Developing leaves, upper surface: Close to 137B. Developing leaves, lower surface: Close to 147B. Fully expanded leaves, upper surface: Close to NN137A; venation, close to 146B. Fully expanded leaves, lower surface: Close to 147B; venation, close to 146B.

*Petioles.*—Length: About 2.5 cm. Diameter: About 3 mm. Texture, upper and lower surfaces: Smooth, glabrous. Color, upper and lower surfaces: Close to 146B.

Inflorescence & flower description:

*Flower type and habit.*—Single fertile and semi-double sterile flowers arranged on large and hemispherical to globose mophead umbels; flowers face upright to somewhat outwardly depending on position on the umbel.

*Fragrance.*—None detected.

*Natural flowering season.*—Continuous and remontant flowering habit from June to August in Grand Haven, Michigan.

*Flower longevity.*—Individual fertile flowers last about two weeks on the plant and are not persistent; individual sterile flowers last about three weeks on the plant and are persistent.

*Quantity of flowers.*—Freely flowering habit; about 30 to 50 fertile flowers and about 400 to 500 sterile flowers develop per inflorescence.

*Inflorescence height.*—About 9 cm.

*Inflorescence diameter.*—About 12 cm.

*Flower diameter, fertile flowers.*—About 5 mm.

*Flower depth (height), fertile flowers.*—About 5 mm.

*Flower diameter, sterile flowers.*—About 2.6 cm.

*Flower depth (height), sterile flowers.*—About 2 cm.

*Flower buds, fertile flowers.*—Length: About 2 mm. Diameter: About 2 mm. Shape: Globose. Color: Close to 144B to 144C.

*Flower buds, sterile flowers.*—Length: About 2 mm. Diameter: About 3 mm. Shape: Globose. Color: Close to 144B to 144C.

*Petals, fertile flowers.*—Quantity and arrangement: About five in a single whorl. Length: About 3 mm. Width: About 2 mm. Shape: Elliptic. Apex: Acute. Base: Truncate. Margin: Entire. Texture, upper and lower surfaces: Smooth, glabrous. Color: When opening, upper and lower surfaces: Close to 65A. Fully opened, upper and lower surfaces: Close to 65A.

*Petals, sterile flowers.*—Quantity and arrangement: About five in a single whorl. Length: About 2 mm. Width: About 1.5 mm. Shape: Elliptic. Apex: Acute. Base: Truncate. Margin: Entire. Texture, upper and lower surfaces: Smooth, glabrous. Color: When opening, upper and lower surfaces: Close to 65A. Fully opened, upper and lower surfaces: Close to 65A.

*Sepals, fertile flowers.*—Quantity and arrangement: About five in a single whorl; fused at the base. Length: About 1 mm. Width: About 0.5 mm. Shape: Elliptic. Apex: Acute. Margin: Entire. Texture, upper and lower surfaces: Smooth, glabrous. Color: When opening, upper and lower surfaces: Close to 144B. Fully opened, upper and lower surfaces: Close to 144B.

*Sepals, sterile flowers.*—Quantity and arrangement: About five to six in about two whorls. Length, inner whorl: About 9 mm. Length, outer whorl: About 1.7 cm. Width, inner whorl: About 9 mm. Width, outer whorl: About 1.9 cm. Shape: Broadly ovate. Apex: Acute. Base: Obtuse. Margin: Entire; slightly undulate. Texture, upper and lower surfaces: Smooth, silky and glabrous. Color: When opening, upper and lower surfaces: Close to 73C to 73D and towards the base, close to 144D. Fully opened, upper and lower surfaces: Close to 73C to 73D; color does not change with subsequent development.

*Pedicels, fertile flowers.*—Length: About 2 mm. Diameter: About 1 mm. Angle: About 45 degrees from peduncle axis. Strength: Strong, flexible. Texture: Smooth, glabrous. Color: Close to 144C and proximally, close to 73C.

*Pedicels, sterile flowers.*—Length: About 1.5 cm. Diameter: About 1 cm. Angle: About 45 degrees from peduncle axis. Strength: Strong, flexible. Texture: Smooth, glabrous. Color: Close to 144C and proximally, close to 73C.

*Reproductive organs, fertile flowers.*—Stamens: Quantity per flower: About five to ten. Filament length: About 3 mm. Filament color: Close to 63B. Anther shape: Rounded; basifixed. Anther length: About 1 mm. Anther color: Close to 70C. Pollen amount: Moderate. Pollen color: Close to 158D. Pistils: Pistil quantity per flower: One. Pistil length: About 2 mm. Stigma shape: Three-lobed. Stigma color: Close to 65A. Style length: Less than 1 mm. Style color: Close to 65A.

*Reproductive organs, sterile flowers.*—Stamens: Quantity per flower: About five to ten. Filament length: About 2 mm. Filament color: Close to 63B. Anther shape: Rounded; basifixed. Anther length: About 1 mm. Anther color: Close to 70C. Pollen amount: Moderate. Pollen color: Close to 158D. Pistils: Pistil quantity per flower: One. Pistil length: About 2 mm. Stigma shape: Two-lobed. Stigma color: Close to 65A. Style length: Less than 1 mm. Style color: Close to 65A.

*Seeds and fruits.*—To date, seed and fruit development has not been observed on plants of the new *Hydrangea.*

Pathogen & pest resistance: To date, plants of the new *Hydrangea* have not been observed to be resistant to pathogens and pests common to *Hydrangea* plants.

Garden performance: Plants of the new *Hydrangea* have been observed to have good garden performance by exhibiting good tolerance to rain and wind and to tolerate temperatures ranging from about −31C to about 38C.

It is claimed:

1. A new and distinct *Hydrangea* plant named 'SMNHMC' as illustrated and described.

* * * * *